(12) United States Patent
Riedemann et al.

(10) Patent No.: US 8,691,251 B2
(45) Date of Patent: Apr. 8, 2014

(54) CORE-SHELL PARTICLES WITH A HIGH CONTENT OF GLYCEROL, THEIR PRODUCTION AND USE

(75) Inventors: Heike Riedemann, Mömbris (DE); Jörg Münzenberg, Hanau (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/490,835

(22) Filed: Jun. 7, 2012

(65) Prior Publication Data

US 2012/0315312 A1 Dec. 13, 2012

Related U.S. Application Data

(60) Provisional application No. 61/607,104, filed on Mar. 6, 2012.

(30) Foreign Application Priority Data

Jun. 9, 2011 (DE) .......................... 10 2011 077 298

(51) Int. Cl.
*A61K 8/02* (2006.01)
*A61K 8/00* (2006.01)
*A61K 47/00* (2006.01)

(52) U.S. Cl.
USPC .......................... 424/401; 424/70.1; 514/770

(58) Field of Classification Search
USPC .................................. 424/401, 70.1; 514/770
See application file for complete search history.

(56) References Cited

U.S. PATENT DOCUMENTS

| 3,393,155 | A  | 7/1968  | Schutte et al. |
| 4,274,883 | A  | 6/1981  | Lumbeck et al. |
| 5,500,223 | A  | 3/1996  | Behan et al. |
| 2004/0180069 | A1 | 9/2004  | Bleuez et al. |
| 2005/0276831 | A1 | 12/2005 | Dihora et al. |
| 2007/0057308 | A1 | 3/2007  | Min et al. |
| 2007/0202063 | A1 | 8/2007  | Dihora et al. |
| 2007/0218024 | A1 | 9/2007  | Zamyatin et al. |
| 2008/0118568 | A1 | 5/2008  | Smets et al. |
| 2008/0187596 | A1 | 8/2008  | Dihora et al. |
| 2009/0202835 | A1 | 8/2009  | Pitsch et al. |
| 2009/0247449 | A1 | 10/2009 | Burdis et al. |
| 2010/0008870 | A1 | 1/2010  | Dihora et al. |
| 2010/0086575 | A1 | 4/2010  | Dihora et al. |

FOREIGN PATENT DOCUMENTS

| DE | 1 467 023 | 1/1969 | |
| DE | 10 2011 077 298.7 | * 6/2011 | ............... A61K 8/02 |
| EP | 0 855 177 | 7/1998 | |
| EP | 1 175 885 | 1/2002 | |
| EP | 1 235 554 | 10/2003 | |
| EP | 1 386 599 | 2/2004 | |
| EP | 1 787 957 A1 | 5/2007 | |
| EP | 1 787 958 A1 | 5/2007 | |
| EP | 1 206 928 | 9/2011 | |
| WO | WO 01/85138 | 11/2001 | |
| WO | WO 2004/010154 | 1/2004 | |
| WO | WO 2006/067235 | 6/2006 | |
| WO | WO 2007/055009 | 5/2007 | |
| WO | WO 2007/057262 | 5/2007 | |
| WO | WO 2007/057308 | 5/2007 | |
| WO | WO 2009/120526 A1 | 10/2009 | |

OTHER PUBLICATIONS

International Search Report issued Oct. 2, 2012 in Application No. PCT/EP2012/059563 (With English Translation of Category of Cited Documents).

* cited by examiner

*Primary Examiner* — Aradhana Sasan
(74) *Attorney, Agent, or Firm* — Oblon, Spivak, McClelland, Maier & Neustadt, L.L.P.

(57) ABSTRACT

The invention relates to core-shell particles, the shell of which includes aggregated, hydrophobicized silicon dioxide particles, and the core of which includes a liquid phase, and in which the ratio of aggregated, hydrobicized silicon dioxide particles to the liquid phase, based on the total weight of the particles, is 2:98 to 40:60, where 60-100% by weight of glycerol is present in the liquid phase. The invention further encompasses the production of these core-shell particles and also their use for cosmetic purposes.

8 Claims, No Drawings

CORE-SHELL PARTICLES WITH A HIGH CONTENT OF GLYCEROL, THEIR PRODUCTION AND USE

BRIEF SUMMARY OF THE INVENTION

The invention relates to core-shell particles, the shell of which comprises aggregated, hydrophobicized silicon dioxide particles, and the core of which comprises a liquid phase. The main constituent of the liquid phase is glycerol. The invention further encompasses the production of these core-shell particles and also their use for cosmetic purposes.

BACKGROUND OF THE INVENTION

DE 1467023 discloses a process for producing so-called "dry water", in which liquid droplets are surrounded by hydrophobicized, pyrogenically produced silicon dioxide particles. As a result of the shell made of silicon dioxide particles, the liquid droplets are prevented from coalescing, and a pulverulent mixture is formed. The water can be released again by rubbing.

EP 0855177 A2 discloses a lightening powder which comprises, inter alia, 0.1-7% by weight of hydrophobicized silica, 5-40% by weight of polyhydric alcohols and 50-94% by weight of water. A higher fraction of polyhydric alcohols is described as being disadvantageous for the skin feel. For a mixture with a water content of less than 50%, incomplete liquidification is predicted.

Encapsulation of a liquid phase by hydrophobicized silicic acid particles, where the liquid phase comprises water as main constituent, has also been disclosed. However, only substances which are soluble in the water phase or are miscible with the water phase can be added to these formulations. Moreover, "dry water" formulations react sensitively to the addition of additives, meaning that in some circumstances no core-shell structure is formed. It follows from this that "dry water" formulations are subject to limitations both with regard to the additives that can be used and also their concentration.

Moreover, "dry water" formulations often have limited stability. In the event of prolonged storage, especially at elevated temperatures, the water enclosed in the shell evaporates. As a result, the composition of the product changes over time. In the case of closed storage of a "dry water", the evaporated water condenses during cooling on the container wall and collects at the bottom of the container, meaning that the "dry water" formulation can no longer be used.

DESCRIPTION OF THE INVENTION

A technical object of the invention is to provide core-shell particles which do not have the above-described disadvantages.

The invention provides core-shell particles, the shell of which comprises aggregated, hydrophobicized silicon dioxide particles, and the core of which comprises a liquid phase, and in which the ratio of aggregated, hydrophobicized silicon dioxide particles to the liquid phase, based on the total weight of the core-shell particles, is 2:98 to 40:60, where 60-100% by weight of glycerol is present in the liquid phase.

The invention also provides a process for producing the core-shell particles, the process comprising charging each constituent of the liquid phase into a container, optionally homogenizing the liquid phase, adding the aggregated, hydrophobicized silicon dioxide particles to the liquid phase to form a mixture, and then shearing the mixture.

The invention further provides a process comprising applying to keratinous material a cosmetic comprising the core-shell particles.

Core-shell particles here means that liquid droplets are surrounded by the aggregated, hydrophobicized silicon dioxide particles, such that particles with a particle size of 0.1-50 μm, preferably from 1-10 μm, are formed. The liquid in the core can either be a solution, an emulsion or a constituent of a dispersion. It is preferably a solution. The shell can be broken open by means of friction, pressure or heat such that the liquid is released and is available for the desired intended use.

Aggregates are to be understood as meaning primary particles joined together firmly, for example by means of sinter necks. The aggregates in turn can cluster together to form agglomerates in which the aggregates are only loosely joined together. Agglomerates can be cleaved again by introducing low shear energies.

The type of aggregated, hydrophobicized silicon dioxide particles is not limited provided it is ensured that when they are added to the liquid phase, core-shell particles are formed. The aggregated, hydrophobicized silicon dioxide particles can preferably be silanized. Halosilanes, alkoxysilanes, silazanes and/or siloxanes can be used for the silanization.

In particular, the following substances can be used as halosilanes:

haloorganosilanes of the type $X_3Si(C_nH_{2n+1})$ where $X=Cl$, Br and $n=1-20$, haloorganosilanes of the type $X_2(R')Si(C_nH_{2n+1})$ where $X=Cl$, Br, R'=alkyl, and $n=1-20$ haloorganosilanes of the type $X(R')_2Si(C_nH_{2n+1})$ where $X=Cl$, Br, R'=alkyl, and $n=1-20$ haloorganosilanes of the type $X_3Si(CH_2)_m$—R' where $X=Cl$, Br, $m=0-20$, R'=alkyl, aryl (for example —$C_6H_5$), —$OCF_2$—CHF—$CF_3$, —$C_6F_{13}$, —O—$CF_2CHF_2$, —$NH_2$, —$N_3$, —SCN, —CH=$CH_2$, —$OC(CH_3)C$=$CH_2$, —$OCH_2$—$CH(O)CH_2$, —NH—COO—$CH_3$, —NH—COO—$CH_2CH_3$, —NH—$(CH_2)_3Si(OR)_3$, —$S_x$—$(CH_2)_3Si(OR)_3$ haloorganosilanes of the type $(R)X_2Si(CH_2)_m$—R' where $X=Cl$, Br, R=alkyl, $m=0-20$, R'=alkyl, aryl (for example —$C_6H_5$), —$C_4F_9$, —$OCF_2$—CHF—$CF_3$, —$C_6F_{13}$, —O—$CF_2$—$CHF_2$, —$NH_2$, —$N_3$, —SCN, —CH=$CH_2$, —$OOC(CH_3)C$=$CH_2$, —$OCH_2$—$CH(O)CH_2$, —NH—COO—$CH_3$, —NH—COO—$CH_2$—$CH_3$, —NH—$(CH_2)_3Si(OR)_3$, —NH—COO—$CH_3$, —NH—COO—$CH_2$—$CH_3$, —NH—$(CH_2)_3Si(OR)_3$, —$(CH_2)_3Si(OR)_3$ haloorganosilanes of the type $(R)_2X\ Si(CH_2)_m$—R' where $X=Cl$, Br, R=alkyl, $m=0-20$, R'=alkyl, aryl (for example —$C_6H_5$), —$OCF_2$—CHF—$CF_3$, —$C_6F_{13}$, —O—$CF_2$—$CHF_2$, —$NH_2$, —$N_3$, —SCN, —CH=$CH_2$, —$OOC(CH_3)$C=$CH_2$, —$OCH_2$—$CH(O)CH_2$, —NH—COO—$CH_3$, —NH—COO—$CH_2$—$CH_3$, —NH—$(CH_2)_3Si(OR)_3$, -Sx-$(CH_2)_3Si(OR)_3$.

In particular, the following substances can be used as alkoxysilanes:

organosilanes of the type $(RO)_3Si(C_nH_{2n+1})$ where R=alkyl, $n=1-20$ organosilanes of the type $R'_x(RO)_ySi(C_nH_{2n+1})$ where R=alkyl, R'=alkyl, $n=1-20$, $x+y=3$, $x=1.2$, $y=1.2$ organosilanes of the type $(RO)_3Si(CH_2)_m$—R' where R=alkyl, $m=0-20$, R'=alkyl, aryl (for example —$C_6H_5$), $OCF_2$—CHF—$CF_3$, —$C_6F_{13}$, —O—$CF_2$—$CHF_2$—, —$NH_2$, —$N_3$, —SCN, —CH=$CH_2$, —$OOC(CH_3)C$=$CH_2$, —$OCH_2$—$CH(O)CH_2$, —NH—COO—$CH_3$, —NH—COO—$CH_2$—$CH_3$, —NH—$(CH_2)_3Si(OR)_3$, —$S_x$—$(CH_2)_3Si(OR)_3$ organosilanes of the type $(R'')_x(RO)_y Si(CH_2)_m$—R' where R''=alkyl, x+y=2, x=1.2, y=1.2, m=0–20, R'=alkyl, aryl (for example —$C_6H_5$), —$OCF_2$—$CHF$—$CF_3$, —$C_6F_{13}$, —O—$CF_2$—$CHF_2$, —$NH_2$, —$N_3$, —SCN, —CH=$CH_2$, —$OOC(CH_3)C$=$CH_2$, —$OCH_2$—$CH(O)CH_2$, NH—COO—$CH_3$, —NH—COO—$CH_2$—$CH_3$, —NH—$(CH_2)_3Si(OR)_3$, —$S_x$—$(CH_2)_3Si(OR)_3$.

Preferably, trimethoxyoctylsilane [$(CH_3O)_3$—Si—$C_8H_{17}$] (for example DYNASYLAN® OCTMO, Evonik Degussa) can be used as silanization agent.

In particular, the following substances can be used as silazanes: silazanes of the type $R'R_2Si$—NH—$SiR_2R'$ where R, R'=alkyl, vinyl, aryl and also, for example, hexamethyldisilazane (for example DYNASYLAN® HMDS, Evonik Degussa).

In particular, the following substances can be used as siloxanes:

cyclic polysiloxanes of the type D 3, D 4, D 5 and their homologues, where D 3, D 4, D 5 are understood as meaning cyclic polysiloxanes having 3, 4 or 5 units of the type —O—$Si(CH_3)_2$, for example octamethylcyclotetrasiloxane=D 4 polysiloxanes and silicone oils of the type Y—O—$[(R^1R^2SiO)_m$—$(R^3R^4SiO)_n]_u$—Y, where m=0, 1, 2, 3, ..., 100000; n=0, 1, 2, 3, ..., 100000; u=0, 1, 2, 3, ..., 100000; $R^1$, $R^2$, $R^3$, $R^4$=independently of one another, alkyl (for example $C_nH_{2n+1}$ where n=1–20), aryl (for example a phenyl radical and/or a substituted phenyl radical), $(CH_2)_n$—$NH_2$, H; and Y=$CH_3$, H, $C_nH_{2n+1}$ where n=2–20, $Si(CH_3)_3$, $Si(CH_3)_2H$, $Si(CH_3)_2OH$, $Si(CH_3)_2(OCH_3)$, $Si(CH_3)_2(C_nH_{2n+1})$ where n=2–20.

The silanization can be carried out by spraying hydrophilic silicon dioxide particles with the silanization agent, which may optionally be dissolved in an organic solvent, such as, for example, ethanol, and then thermally treating the mixture at a temperature from 105 to 400° C. over a period of 1 to 6 h.

Preferably, silicon dioxide particles of pyrogenic origin can be used. Pyrogenic here encompasses those particles which are obtainable from suitable silicon compounds by means of flame oxidation or flame hydrolysis. As a rule, silicon tetrachloride is hydrolysed to silicon dioxide in a flame of hydrogen and oxygen.

As a rule, the methanol wettability is determined as a measure of the hydrophobicity. The aggregated, hydrophobicized silicon dioxide particles preferably have a methanol wettability of at least 35% by volume of methanol, preference being given to values of 38 to 75% by volume of methanol. When determining the methanol wettability, in each case 0.2 g f 0.005 g of aggregated, hydrophobicized silicon dioxide particles are weighed into transparent centrifuge tubes. 8.0 ml of a methanol/water mixture with in each case 10, 20, 30, 40, 50, 60, 70 and 80% by volume of methanol are added to each initial weighing. The closed tubes are shaken for 30 seconds and then centrifuged for 5 minutes at 2500 rpm. The sediment volumes are read off, converted to a percentage and plotted on a graph against the methanol content in percent by volume. The point of inflection of the curve corresponds to the methanol wettability.

Preferably, the silicon dioxide particles hydrophobicized with octamethylcyclotetrasiloxane, polydimethylsiloxane, octylsilane and/or hexamethyldisilazane can be used, with hexamethyldisilazane being particularly preferred.

The specific surface area of the aggregated, hydrophobicized silicon dioxide particles is not limited. Preferably, the core-shell particles according to the invention comprise those silicon dioxide particles with a specific surface area of from 80 to 300 $m^2/g$ and particularly preferably those from 100 to 250 $m^2/g$, the specific surface area being very particularly preferably 220±25 $m^2/g$. The BET surface area is determined in accordance with DIN 66131.

Examples of commercially available aggregated, hydrophobicized silicon dioxide particles are AEROSIL® R 202, AEROSIL® R 805, AEROSIL® R 812, AEROSIL® R 812 S, AEROSIL® R 972, all from Evonik Degussa. The properties of the silicon dioxide particles can be found in Table 1.

Based on the total weight of the core-shell particles according to the invention, the content of aggregated, hydrophobicized silicon dioxide particles is 2-40% by weight, preferably 2-20% by weight, very particularly preferably 2-15% by weight.

The core-shell particles according to the invention comprise aggregated, hydrophobicized silicon dioxide particles and glycerol, where glycerol is present in the liquid phase with a fraction of 60-100% by weight. Preferably, glycerol is present in the liquid phase with a weight fraction of 75-99.5%, particularly preferably a fraction of 85-95% by weight. In a particular embodiment, the liquid phase consists entirely of glycerol.

Besides glycerol, the core-shell particles according to the invention can comprise up to 40% by weight of water in the liquid phase, preferably up to 20% by weight, particularly preferably up to 10% by weight. In one particular embodiment, the liquid phase does not comprise any water.

Moreover, cosmetic auxiliaries and/or active ingredients which the person skilled in the art knows from the field of "dry water" may additionally be present in the liquid phase. These substances can belong to the following groups: UV photoprotective filters, dyes and pigments, deodorant and antiperspirant active ingredients, biogenic substances, insect repellent active ingredients, hydrotropes, antidandruff active ingredients, bleaches or skin lightening agents, and also self-tanning agents, preservatives, surfactants/emulsifiers, perfume oils and plant extracts, active ingredients, film formers, oils, emollients and inorganic salts.

The fraction of cosmetically relevant auxiliaries and active ingredients can together be up to 25% by weight, based on the liquid phase. Preference is given to weight fractions of below 15% by weight, particularly preferably 0.1-10% by weight, in each case based on the liquid phase.

Inorganic salts which can be used are in particular the halides, carbonates, hydrogencarbonates, borates, sulphates, phosphates, hydrogenphosphates, nitrates, nitrites, silicates or ammonium salts of alkali metal and alkaline earth metal ions. Very particular preference is given to at least one of the following salts: NaCl, KCl, $MgSO_4$, $MgCl_2$, $CaCl_2$, $NaHCO_3$. Salts are used with a total concentration of up to 5% by weight in aqueous solution, based on the total weight of the solution, particular preference being given to a total concentration of 0.1-3.5% by weight.

Moreover, the following substances are particularly suitable: aluminium chlorohydrate (LOCRON® P), vitamin. E acetate, perfume oils, pigments, vinylpyrrolidone-vinyl acetate copolymer (KOLLIDON®, VP/VA copolymer), aloe vera, and also, as emollient, TEGOSOFT® GMC 6, ABIL®B 8843 or ABIL® B 8852, all three Evonik Goldschmidt.

The addition of auxiliaries and/or active ingredients can influence the surface tension of the liquid phase. The surface tension value of the liquid phase of the core-shell particles according to the invention at 25° C. should generally be 55-75 mN/m. Preferably, the surface tension is 60-67 mN/m, particular preference being given to values of 62-65 mN/m, in each case at 25° C. The surface tension is determined in accordance with the ring method (ISO 304).

The invention further provides a process for producing the core-shell particles, in which the constituents of the liquid phase are firstly introduced as initial charge and are optionally homogenized, then the aggregated, hydrophobicized silicon dioxide particles are added and the mixture is sheared.

The invention further provides a hair-styling powder comprising the core-shell particles. Here, a hair-styling powder is to be understood as meaning a powder for the temporary shaping of human hair.

The invention further encompasses the use of the core-shell particles for cosmetic purposes.

EXAMPLES

The experiments were all carried out with DAB glycerol with a glycerol content of 99.5%. The aggregated, hydrophobicized silicon dioxide particles used all originate from Evonik Degussa.

General procedure: The core-shell particles according to the invention were obtained by firstly introducing the constituents of the liquid phase as an initial charge and optionally homogenizing them, then adding the aggregated, hydrophobicized silicon dioxide particles, and shearing the mixture. The product obtained was decanted into plastic containers. The consistency of the product was assessed visually. The quantitative data and shear parameters used can be found in Table 2.

Example 1

98 g of glycerol was introduced as an initial charge in a 500 ml stainless steel beaker of the DISPERMAT® CA-40 M1 dissolver (VMA-Getzmann GmbH, plate diameter 5 cm). Then, 2 g of AEROSIL® R 812 S was added. The mixing beaker was closed with a lid. The shearing was carried out for 2 minutes at 3000 rpm. Pulverulent, free-flowing core-shell particles were produced.

Examples 2 to 14 were prepared analogously to Example 1.

Examples 2 to 12 each produced pulverulent, free-flowing core-shell particles, whereas comparative examples 13 and 14 each produced a cream.

The properties of the core-shell particles were assessed visually.

TABLE 1

Silicon dioxide particles used

| Hydrophobicized silicon dioxide | Hydrophobicization agent | Spec. surface area (BET) $m^2/g$ | Methanol wettability [% by volume of methanol] | Carbon content (% by weight) |
| --- | --- | --- | --- | --- |
| AEROSIL ® R 812 S | hexamethyldisilazane | 220 ± 25 | 52-60 | 3.0-4.0 |
| AEROSIL ® R 805 | octylsilane | 150 ± 25 | 45 | 4.5-6.5 |
| AEROSIL ® R 202 | polydimethylsiloxane | 100 ± 20 | 70 | 3.5-5.0 |
| AEROSIL ® R 972 | dimethyldichlorosilane | 110 ± 20 | 38 | 0.6-1.2 |

TABLE 2

Composition and properties of the exemplary formulations

| Example | AEROSIL ® R | [g] | Glycerol [g] | Water [g] | Addition [g] | Process [rpm]/[min] | Property |
| --- | --- | --- | --- | --- | --- | --- | --- |
| 1 | 812 S | 2 | 98 | — | — | 3000/2 | powder, free-flowing |
| 2 | 812 S | 5 | 95 | — | — | 3000/3 | powder, free-flowing |
| 3 | 972 | 5 | 95 | — | — | 3000/3 | powder, free-flowing |
| 4 | 805 | 5 | 95 | — | — | 3000/3 | powder, free-flowing |
| 5 | 202 | 5 | 95 | — | — | 5000/5 | powder, free-flowing |
| 6 | 812 S | 5 | 66.5 | 28.5 | — | 6000/6 | powder, free-flowing |
| 7 | 812 S | 5 | 90 | — | pigment mixture[1] 5 | 3000/2 | powder, free-flowing |
| 8 | 812 S | 5 | 76 | — | Locron ® P, 19 | 3000/3 | powder, free-flowing |
| 9 | 812 S | 10 | 87.6 | — | PEG-6, 2.7 | 3000/2 | powder, free-flowing |
| 10 | 812 S | 5 | 94.05 | — | VP/VA-copolymer, 0.95 | 3000/2 | powder, free-flowing |
| 11 | 812 S | 5 | 66.5 | — | salt water (3.5% strength), 28.5 | 3000/3 | powder, free-flowing |
| 12 | 812 S | 10 | 89 | — | beeswax, 1 | 4000/3 | powder, free-flowing |
| 13 | 812 S | 5 | — | — | ethylene glycol, 95 | 3000/3 | white cream |
| 14 | 812 S | 5 | — | — | polyethylene glycol, 95 | 2500/5 | clear cream |

[1]W1802 Pigment Jaune Covasil S, INCI: CI 77492, trimethoxycaprylylsilane 45% by weight, W3801 Pigment Rouge Covasil S, INCI: CI 77491, trimethoxycaprylylsilane 15% by weight, W9814 Pigment Noir Covasil S, INCI: CI 77499, trimethoxycaprylylsilane 10% by weight, Oxyde de Titane STD Covasil, INCI: CI 77891, trimethoxycaprylylsilane 30% by weight, all from Sensient Cosmetic Technologies

The invention claimed is:

1. A core-shell particle comprising a shell and a core, wherein the shell comprises silanized, aggregated, hydrophobicized silicon dioxide particles and the core comprises a liquid phase, and wherein the ratio of silanized, aggregated, hydrophobicized silicon dioxide particles to the liquid phase, based on the total weight of the particles, is 2:98 to 40:60, wherein 60-100% by weight of glycerol is present in the liquid phase, up to 10% by weight of water is present in the liquid phase, and one or more cosmetic active ingredients are additionally present in the liquid phase.

2. The core-shell particle according to claim 1, wherein one or more cosmetic auxiliaries are additionally present in the liquid phase.

3. The core-shell particle according to claim 2, wherein the weight fraction of the cosmetic auxiliaries and the cosmetic active ingredients together is up to 25% by weight, based on the liquid phase.

4. The core-shell particle according to claim 1, wherein the surface tension of the liquid phase at 25° C. is 55-75 mN/m.

5. A process for producing the core-shell particle according to claim 1, comprising:
    charging each constituent of the liquid phase into a container,
    optionally, homogenizing the liquid phase,
    adding the silanized, aggregated, hydrophobicized silicon dioxide particles to the liquid phase to form a mixture, and
    shearing the mixture.

6. A hair-styling powder comprising core-shell particles according to claim 1.

7. A process comprising applying to keratinous material a cosmetic comprising core-shell particles according to claim 1.

8. The core-shell particle according to claim 2, wherein the one or more cosmetic active ingredients and the one or more cosmetic auxiliaries are selected from the group consisting of UV photoprotective filters, UV photoprotective dyes, UV photoprotective pigments, deodorant active ingredients, antiperspirant active ingredients, biogenic substances, insect repellent active ingredients, hydrotropes, antidandruff active ingredients, bleaches, skin lightening agents, self-tanning agents, preservatives, surfactants/emulsifiers, perfume oils, plant extracts, film formers, oils, emollients and inorganic salts.

* * * * *